US012685738B2

(12) United States Patent
Lee et al.

(10) Patent No.: US 12,685,738 B2
(45) Date of Patent: Jul. 21, 2026

(54) INOTODIOL AS AGONIST OF LIVER X RECEPTORS, AND USE THEREOF

(71) Applicant: CARBOEXPERT INC., Daejeon (KR)

(72) Inventors: Chang Kyu Lee, Daejeon (KR); So Young Ban, Daejeon (KR); Kyubeen Park, Sejong (KR); Nan Young Lee, Daejeon (KR); Hyunah Park, Daejeon (KR); Wonhee Lee, Sejong (KR)

(73) Assignee: CARBOEXPERT INC., Daejeon (KR)

( * ) Notice: Subject to any disclaimer, the term of this patent is extended or adjusted under 35 U.S.C. 154(b) by 619 days.

(21) Appl. No.: 18/019,598

(22) PCT Filed: Aug. 6, 2021

(86) PCT No.: PCT/KR2021/010447
§ 371 (c)(1),
(2) Date: Feb. 3, 2023

(87) PCT Pub. No.: WO2022/031129
PCT Pub. Date: Feb. 10, 2022

(65) Prior Publication Data

US 2023/0302017 A1 Sep. 28, 2023

(30) Foreign Application Priority Data

Aug. 6, 2020 (KR) ........................ 10-2020-0098809

(51) Int. Cl.
*A61K 31/575* (2006.01)
*A61P 17/06* (2006.01)
*A61P 19/02* (2006.01)
*A61P 25/28* (2006.01)

(52) U.S. Cl.
CPC ............ *A61K 31/575* (2013.01); *A61P 17/06* (2018.01); *A61P 19/02* (2018.01); *A61P 25/28* (2018.01)

(58) Field of Classification Search
CPC .................................................... A61K 31/575
See application file for complete search history.

(56) References Cited

FOREIGN PATENT DOCUMENTS

| | | | |
|---|---|---|---|
| CN | 109985051 | A | 7/2019 |
| KR | 10-2005-0019433 | A | 3/2005 |
| KR | 10-1893754 | B1 | 8/2018 |
| KR | 10-2018-0099052 | A | 9/2018 |
| WO | 2019/225783 | A1 | 11/2019 |

OTHER PUBLICATIONS

Jasim, The emerging role of 27 hydroxycholesterol in cancer development and progression: An update, International Immunopharmacology vol. 110, Sep. 2022, 109074.*
Ramalingam, Liver X Receptors (LXRs) in cancer—an Eagle's view on molecular insights and therapeutic opportunities Front Cell Dev Biol. Mar. 14, 2024;12:138610.*
Zhang, Journal of Neuroinflammation (2024) 21:97, 1-13.*
Wolff, Burger's medicinal Chemistry and Drug Discovery, vol. 1, Principles and Practice, John Wiley & sons, New York, 1997.*
Akita, Journal of Pharmacy and Nutrition Sciences (2015), 5(1), 71-76.*
Lu, Journal of the Science of Food and Agriculture (2010), 90(2), 276-280.*
Zhang Xu, Nat Prod Res Dev (2010), 22(3), 433-436.*
Nguyen, Anti-allergic effect of inotodiol, a lanostane triterpenoid from Chaga mushroom, via selective inhibition of mast cell functionInternational Immunopharmacology 81 (2020) 106244.*
Burns, European Journal of Pharmacology vol. 759, Jul. 15, 2015, pp. 101-117.*
Perlman Evolution, Medicine, and Public Health [2016] pp. 170-176.*
Jiang et al., "ApoE Promotes the Proteolytic Degradation of Abeta," Neuron, 58: 681-693 (2008).
Zhang et al., "Inotodiol suppresses proliferation of breast cancer in rat model of type 2 diabetes mellitus via downregulation of beta-catenin signaling," Biomedicine & Pharmacotherapy, 99: 142-150 (2018).
Caldas et al., "Liver X receptor-activating ligands modulate renal and intestinal sodium-phosphate transporters," Kidney International, 80: 535-544 (2011).
Cao et al., "Liver X Receptor-Mediated Gene Regulation and Cholesterol Homeostasis in Brain: Relevance to Alzheimer's Disease Therapeutics," Current Alzheimer Research, 4: 179-184 (2007).
Kleyer et al., "Liver X Receptors Orchestrate Osteoblast/Osteoclast Crosstalk and Counteract Pathologic Bone Loss," Journal of Bone and Mineral Research, 27 (12): 2442-2451 (2012).
Michael et al., "Liver X Receptors, Atherosclerosis and Inflammation," Current Atherosclerosis Reports, 14: 284-293 (2012).
Nakata et al., "Structure determination of inonotsuoxides A and B and in vivo anti-tumor promoting activity of inotodiol from the sclerotia of Inonotus obliquus," Bioorganic & Medicinal Chemistry, 15: 257-264 (2007).
International Search Report issued in corresponding International Patent Application No. PCT/KR2021/010447 dated Dec. 6, 2021.
Jayasuriya et al., "Diterpenoid, Steroid, and Triterpenoid Agonists of Liver X Receptors from Diversified Terrestrial Plants and Marine Sources", J. Nat. Prod., vol. 68, 2005, pp. 1247-1252.
Loren et al., "Liver X receptor modulators: a review of recently patented compounds (2009-2012)", Expert Opinion on Therapeutic Patents, vol. 23, No. 10, 2013, pp. 1317-1335.
Tice et al., "The Medicinal Chemistry of Liver X Receptor (LXR) Modulators", Journal of Medicinal Chemistry, vol. 57, 2014, pp. 7182-7205.
Yu et al., "Dissociated sterol-based liver X receptor agonists as therapeutics for chronic inflammatory diseases", FASEB J., vol. 30, 2016, pp. 2570-2579.

* cited by examiner

*Primary Examiner* — Nizal S Chandrakumar
(74) *Attorney, Agent, or Firm* — Morgan, Lewis & Bockius LLP

(57) ABSTRACT

The present disclosure relates to inotodiol as a liver X receptor agonist and use thereof for the treatment of a liver X receptor-mediated disease. Inotodiol according to an aspect, or a prodrug thereof has LXRβ-specific agonist activity, and thus not only has remarkable safety compared to other LXR agonists, but can also be effectively used in the treatment of LXR-related diseases, such as a neurodegenerative brain disease, an autoimmune disease, NASH, and NAFLD.

5 Claims, 9 Drawing Sheets

INOTODIOL AS AGONIST OF LIVER X RECEPTORS, AND USE THEREOF

TECHNICAL FIELD

The present disclosure relates to inotodiol as a liver X receptor agonist and use thereof for the treatment of a liver X receptor-mediated disease.

BACKGROUND ART

Liver X receptors (LXRs) are ligand-activated transcription factors that play a crucial role in regulating the expression of genes involved in lipid metabolism and cellular cholesterol homeostasis. LXR agonists have been shown to enhance reverse cholesterol transport (RCT), enabling RCT from the periphery back to the liver for processing and excretion. RCT occurs via upregulation of cholesterol transporter proteins (ATP-binding cassettes: ABCA1 and ABCG1) in peripheral phagocytes. Active RCT has been reported to have the potential to inhibit the progression of atherosclerosis.

There are two isoforms of LXR, i.e., LXRα (NR1H3) and LXRβ (NR1H2), encoded by separate genes. LXRβ is commonly expressed in most tissues, whereas LXRα expression is tissue-selective and LXRα is expressed in the liver, small intestine, kidney, adipose tissue and adrenal glands, which are important for lipid homeostasis. Both LXRs require the retinoid X receptor (RXR) as an obligate heterodimer partner to recognize and bind cooperatively to LXR response elements (LXREs) consisting of two direct repeats of a core hexameric sequence spaced by four nucleotides (DR4). The ligand-binding domains of the two LXRs are fairly well conserved (~78% amino acid homology) and bind to endogenous ligands consisting of oxidized derivatives of cholesterol (oxysterols) that serve as intermediates in steroid hormone and bile acid synthesis. Among these, 22(R)-hydroxycholesterol, 24(S)-hydroxycholesterol, and 24(S),25-epoxycholesterol have been reported as the most potent ligands. These data suggest an important role for LXRs in maintaining cholesterol homeostasis, which was later confirmed through gene knock-out studies in mice. Non-steroidal ligands have been identified, and, using these as chemical probes, many LXR-regulated genes have been discovered. Several LXRE-containing genes are involved in cholesterol metabolism, reverse cholesterol transport (RCT) and lipogenesis. Other genes are involved in inflammation and carbohydrate metabolism-deficient LXREs, but are suppressed by LXRs in a ligand-dependent manner. Based on these findings, the liver X receptors have recently emerged as excellent targets acting as intracellular cholesterol sensors, providing the basis for the treatment of a variety of diseases, including atherosclerosis, diabetes, Alzheimer's disease, skin disorders, reproductive diseases, and cancer (Viennois et al., 2011, Expert Opin. Ther. Targets, 15(2): 219-232). Additionally, it has been discovered that LXR agonists modulate intestinal and renal sodium phosphate (NaPi) transporters and, in turn, serum phosphate levels (Caldas et al., 2011, Kidney International, 80:535-544). Thus, LXR may also be a target for kidney disorders, and particularly for the prevention of hyperphosphatemia and associated cardiovascular complications. In addition, LXRs are recognized as targets in the treatment of osteoporosis and related diseases. (Kleyer et al., 2012, J. Bone Miner. Res., 27(12):2442-51).

Alzheimer's disease is one of the most common forms of dementia and is characterized by the accumulation and deposition of amyloid-beta (Aβ) peptides in the brain, leading to the perturbation of synaptic function and neuronal loss in the brains of affected individuals. Neurons in the brain produce amyloid-beta (Aβ) peptides via cleavage of amyloid precursor protein (APP), and amyloid-beta (Aβ) peptides are normally eliminated through efflux into the peripheral circulation and by action by proteinases within the brain.

Apolipoprotein E (apoE) is associated with age-related risk for Alzheimer's disease and plays a decisive role in Aβ homeostasis. LXR increases the expression of apoE and increases the lipidation of apoE. The degradation of Aβ both intracellularly and extracellularly is enhanced by lipidated apoE. LXR agonist treatment promoted proteolytic degradation of Aβ, reduced plaque disease, and improved memory in APP-expressing transgenic mice (Jiang et al., 2008, Neuron, 58: 681-693).

Therefore, there is a need to develop treatments for LXR-mediated diseases, for example, arteriosclerosis, Alzheimer's disease and metabolic diseases, through the development of LXR agonists.

DETAILED DESCRIPTION OF DISCLOSURE

Technical Problem

One aspect is to provide a liver X receptor (LXR) agonist including inotodiol, a prodrug thereof, or a pharmaceutically acceptable salt thereof as an active ingredient.

Another aspect is to provide a pharmaceutical composition for the prevention or treatment of a liver X receptor (LXR)-mediated disease, including inotodiol, a prodrug thereof, or a pharmaceutically acceptable salt thereof as an active ingredient.

Another aspect is to provide use of inotodiol, a prodrug thereof or a pharmaceutically acceptable salt thereof for the preparation of a liver X receptor (LXR) agonist or a therapeutic agent for an LXR-mediated disease.

Another aspect is to provide a method of upregulating liver X receptors (LXRs), including administering inotodiol, a prodrug thereof, or a pharmaceutically acceptable salt thereof to a subject in need thereof, and a method of treating an LXR-mediated disease.

Another aspect is to provide a health functional food for the prevention or amelioration of a liver X receptor (LXR)-mediated disease, including inotodiol, a prodrug thereof, or a pharmaceutically acceptable salt thereof as an active ingredient.

Another aspect is to provide a cosmetic composition for the prevention or amelioration of liver X receptor (LXR)-mediated skin conditions, including inotodiol, a prodrug thereof, or a pharmaceutically acceptable salt thereof as an active ingredient.

Technical Solution

One aspect provides a liver X receptor (LXR) agonist including inotodiol, a prodrug thereof, or a pharmaceutically acceptable salt thereof as an active ingredient.

Another aspect provides a pharmaceutical composition for the prevention or treatment of a liver X receptor (LXR)-mediated disease, including inotodiol, a prodrug thereof, or a pharmaceutically acceptable salt thereof as an active ingredient.

Another aspect provides use of inotodiol, a prodrug thereof or a pharmaceutically acceptable salt thereof for the preparation of a liver X receptor (LXR) agonist, or a therapeutic agent for an LXR-mediated disease.

Another aspect provides a method of upregulating liver X receptors (LXRs), including administering inotodiol, a prodrug thereof, or a pharmaceutically acceptable salt thereof to a subject in need thereof, and a method of treating an LXR-mediated disease.

The term "inotodiol" as used herein has the IUPAC name of (3S,5R,10S,13R,14R,17R)-17-[(2S,3R)-3-hydroxy-6-methylhept-5-en-2-yl]-4,4,10,13,14-pentamethyl-2,3,5,6,7,11,12,15,16,17-decahydro-1H-cyclopenta[a]phenanthren-3-ol.

The inotodiol is a major physiologically active ingredient of Inonotus obliquus, and may be chemically synthesized according to a general method, may be prepared as a pharmaceutically acceptable salt, or may be separated and purified from an Inonotus obliquus extract.

The inotodiol or the prodrug thereof acts as a liver X receptor (LXR) agonist.

Provided herein is a method of treating a subject having a disease or disorder treatable by an LXR agonist. In one embodiment, LXRs may be regulated by upregulating the activity thereof. The method includes administering an effective amount of inotodiol or a prodrug thereof.

The method or the pharmaceutical composition provided herein may be useful for disorders that can be treated by modulating LXRs, particularly in the case of LXR agonists.

In one embodiment, inotodiol or a prodrug thereof is useful for the treatment or treatment of diseases or disorders associated with altered cholesterol transport, fatty acid metabolism, cholesterol absorption, cholesterol reabsorption, cholesterol secretion, cholesterol excretion, or cholesterol metabolism. Representative diseases or disorders include: lipid disorders; cancer, particularly hormone-dependent cancer including ovarian cancer, breast cancer, and prostate cancer; acne skin conditions; skin inflammatory disease; immune disorders; conditions characterized by disrupted epidermal barrier function; disturbed differentiation or excess proliferation of the epidermis or mucous membrane; cardiovascular disorders; reproductive tract disorders; optic nerve and retinal abnormalities; neurodegenerative disorders arising from diseases; central or peripheral nervous system damage; neuropathic diseases; degenerative processes due to aging; diseases or disorders of the kidneys; and osteoporosis and related diseases, but the present disclosure is not limited thereto.

In another embodiment, the disease or the disorder is a neurodegenerative brain disease, an autoimmune disease, hyperlipidemia, hypercholesterolemia, hyperlipoproteinemia, hypertriglyceridemia, lipodystrophy, hepatic steatosis, nonalcoholic steatohepatitis (NASH), nonalcoholic fatty liver disease (NAFLD), hyperglycemia, insulin resistance, diabetes mellitus, dyslipidemia, atherosclerosis, gallstone disease, acne vulgaris, dermatitis (not limited to psoriasis and contact dermatitis), hyperphosphatemia, related cardiovascular complications of hyperphosphatemia, cancer, multiple sclerosis, or osteoporosis.

In another embodiment, the disease and the disorder are: common acne; comedones; polymorphs; rosacea; nodulocystic acne; acne conglobate; senile acne; secondary acne including, but not being limited to, solar, medicinal and occupational acne; ichthyosis; ichthyosiform conditions; Darier's disease; palmoplantar keratoderma; leukoplakia; leukoplakiform conditions; cutaneous or mucous (oral) lichen; dermatological conditions or afflictions with an inflammatory immunoallergic component, with or without a cellular proliferation disorder, including, but not being limited to, cutaneous psoriasis, mucous psoriasis, ungual psoriasis, psoriatic rheumatism, and cutaneous atopy, and including eczema, respiratory atopy, and gingival hypertrophy; benign or malignant dermal or epidermal proliferations, of viral or non-viral origin, including, but not being limited to, common warts, flat warts, epidermodysplasia verruciformis, oral or florid papillomatoses, and T lymphoma or cutaneous T-cell lymphoma; proliferations induced by ultraviolet light, including, but not being limited to, basocellular epithelioma and spinocellular epithelioma; precancerous skin lesions, including, but not being limited to, keratoacanthomas; immune dermatitides, including, but not being limited to, lupus erythematosus; bullous immune diseases; collagen diseases including, but not being limited to, scleroderma; dermatological or systemic conditions or afflictions with an immunological component; skin disorders due to exposure to UV radiation; photo-induced or chronological aging of the skin; actinic pigmentations; keratosis; pathology associated with chronological or actinic aging, including, but not being limited to, zerosis; sebaceous function disorders including, but not being limited to, hyperseborrhoea of acne, simple seborrhoea, and seborrhoeic dermatitis; cicatrization disorders including, but not being limited to, stretch marks; pigmentation disorders including, but not being limited to, hyperpigmentation, melasma, hypopigmentation, and vitiligo; and alopecia including, but not being limited to, chemotherapy-associated alopecia and radiation-associated alopecia.

In another embodiment, the disease or disorder is a neurodegenerative brain disease or an autoimmune disease.

The neurodegenerative brain disease may be selected from the group consisting of dementia, Alzheimer's disease, Parkinson's disease, Huntington's disease, mild cognitive impairment, cerebral amyloid angiopathy, Down's syndrome, amyloidogenic stroke, systemic amyloid disease, Dutch-type amyloidosis, Niemann-Pick disease, senile dementia, amyotrophic lateral sclerosis, spinocerebellar atrophy, Tourette's syndrome, Friedrich's ataxia, Machado-Joseph's disease, Lewy body dementia, dystonia, progressive supranuclear palsy, and frontotemporal dementia.

The autoimmune disease may be selected from the group consisting of rheumatoid arthritis, psoriasis, dermatitis, multiple sclerosis, and diabetes mellitus. The dermatitis may include atopy, acne, contact dermatitis, and the like.

The inventors of the present disclosure confirmed that inotodiol was effectively delivered to the brain of animals and increased the expression of ABCA1 and APOE genes known as factors that eliminate inflammation and amyloid beta in the brain, through which it was confirmed that inotodiol could be effectively used in the prevention or treatment of a neurodegenerative brain disease.

It was also confirmed that inotodiol had an arthritis alleviating effect in an arthritis animal model and lowered the expression of TNF-α, through which it was confirmed that inotodiol could be effectively used in the prevention or treatment of autoimmune diseases such as psoriasis and dermatitis, as well was arthritis.

In one embodiment, the prodrug of inotodiol may be an inotodiol ester derivative compound formed through an ester condensation reaction between a hydroxyl group of an inotodiol compound represented by Formula 1 below and a carboxyl group of a fatty acid, glucuronic acid, alkyl succinic anhydride, or phenolic acid:

[Formula 1]

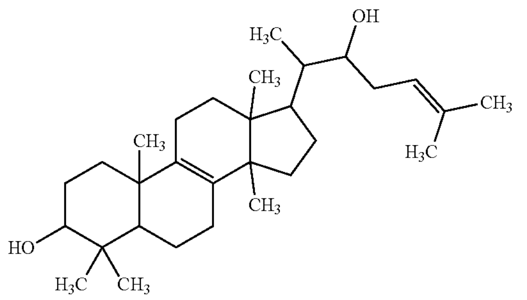

Particularly, the prodrug may be a compound represented by Formula 2 below:

[Formula 2]

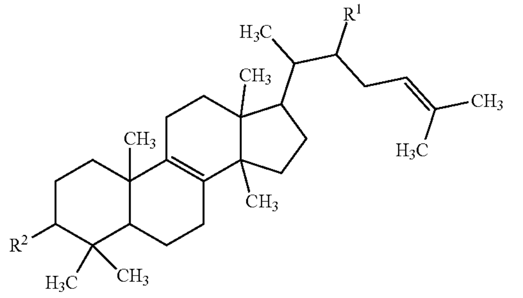

wherein, in Formula 2, R1 and R2 are each independently OH, or —OC(O)—R3 wherein R3 is a linear or branched alkyl, alkenyl or alkynyl chain having 1 to 30, 4 to 30, or 6 to 30 carbon atoms, and at least one of R1 and R2 is —OC(O)—R3.

In one embodiment, R3 is an unsubstituted linear alkyl or alkenyl chain having $CH_3(CH_2)_a$— or $CH_3(CH_2)_b(CH{=}CH[CH_2])_c(CH_2)_d$— wherein a is an integer of 8 to 24, b is an integer of 1 to 5, c is an integer of 1 to 6, and d is an integer of 3 to 7.

The term "prodrug" as used herein may refer to a drug that itself may be biologically inactive, but exhibits an effective medicinal effect after chemical/biochemical structural transformation during the residence time thereof in the body. That is, prodrugs are those that are made possible for clinical use by imparting chemical modification to those having unsuitable properties in terms of side effects, stability, solubility, absorption, and duration of action, although these are useful drugs. An inotodiol derivative according to one embodiment is a compound formed through an ester bond between inotodiol and a fatty acid, and has increased solubility in an organic solvent and improved stability, and is easily decomposed into inotodiol and a fatty acid in the small intestine, thus facilitating absorption into the small intestine. For example, the inotodiol derivative may be formed through an ester bond between inotodiol and succinic acid. Specifically, the inotodiol derivative may be synthesized through a condensation reaction between alkyl succinic anhydride and inotodiol in the presence of a p-toluene sulfonic acid catalyst, and a succinic acid ester bond may be induced to all or one or more hydroxyl groups of inotodiol by adding alkyl succinic anhydride in an excess amount compared to inotodiol. After the reaction is completed, p-toluene sulfonic acid is neutralized with sodium bicarbonate and removed. In the inotodiol derivative compound synthesized by the above method, both or at least one of R1 and R2 of Formula 2 form a succinic acid ester bond, whereby water solubility is improved, and the ester bond is easily decomposed, thus being easily absorbed into the small intestine. In addition, in an inotodiol derivative according to another embodiment, the water solubility of inotodiol is increased through an ester bond between inotodiol and a fatty acid, and hydrolysis in the small intestine and absorption into the body are reduced, thereby increasing the probability that the inotodiol derivative can reach the large intestine. Thus, when the inotodiol derivative is decomposed by various microorganisms in the large intestine, inotodiol can exhibit direct pharmacological activity. For example, the inotodiol derivative may be formed through an ester bond between inotodiol and phenolic acid. Specifically, the ester bond of the inotodiol derivative is hydrolyzed in the large intestine to release inotodiol and phenolic acid, and accordingly, various physiological activities of each of inotodiol and phenolic acid can be expected. Therefore, the prodrug according to one aspect enables a reduced dosage of inotodiol and can reduce side effects that may occur when ingested at a high dose.

The prodrug derivative of inotodiol may be synthesized through a chemical or biological method. Specifically, the inotodiol derivative may be synthesized by an esterification reaction between inotodiol and a fatty acid. The fatty acid may be a $C_{10}$-$C_{30}$ unsaturated or saturated fatty acid, and may be selected from the group consisting of $C_1$-$C_{10}$ carboxylic acids or phenolic acids. Examples of the unsaturated fatty acid may include myristoleic acid, palmitoleic acid, sapienic acid, oleic acid, elaidic acid, vaccenic acid, linoleic acid, linoelaidic acid, arachidonic acid, eicosapentaenoic acid, erucic acid, and docosahexaenoic acid. Examples of the saturated fatty acid may include caprylic acid, capric acid, lauric acid, palmitic acid, stearic acid, arachidic acid, behenic acid, lignoceric acid, cerotic acid, and myristic acid. The saturated carboxylic acids may be, for example, formic acid, acetic acid, propionic acid, butyric acid, and succinic acid. The phenolic acids may be, for example, p-coumaric acid, cinnamic acid, ferulic acid, 3,4-dihydroxy benzoic acid, p-hydroxy benzoic acid, vanilic acid, caffeic acid, syringic acid, and sinapinic acids. In one embodiment, the inotodiol derivative may be synthesized by mixing, in a molar ratio of 1:10-30, inotodiol and a fatty acid selected from the group consisting of an unsaturated fatty acid, a saturated fatty acid, and a $C_1$-$C_{10}$ carboxylic acid. For example, the mixing may be performed in a molar ratio of 1:10-30, 1:10-25, 1:10-20, 1:10-15, 1:10-13, 5:10-30, or 5:10-15. In this case, when the mixing ratio of inotodiol and the fatty acid is less than or exceeds the above range, the reaction does not sufficiently occur, resulting in reduced production efficiency of the inotodiol derivative or increased reaction time. In addition, the esterification reaction may be carried out at 55° C. to 65° C. for 48 hours to 96 hours. In this case, when the esterification reaction conditions are less than or exceed the above ranges, it is difficult to completely dissolve the fatty acid, which is a reaction substrate, and thus the reaction hardly occurs, or the esterification reaction efficiency is lowered due to reduced enzymatic activity, and thus, there is a problem in that the inotodiol derivative, which is a final product, cannot be synthesized with a high yield. In addition, after the esterification reaction is completed, the purity of an ester included in the product may be further increased through various known distillation or purification methods.

In addition, the inotodiol derivative may be synthesized by adding a biological enzyme to a mixture of inotodiol and a fatty acid, and the biological enzyme is an enzyme suitable for producing a high-efficiency inotodiol derivative and may be, for example, *Candida antarctica* lipase B (CalB). To increase the yield of the inotodiol derivative, which is a final product, the *Candida antarctica* lipase B may be an immobilized enzyme, rather than a general enzyme, and the immobilized enzyme may be a commercially available product or an enzyme prepared by a general method. In addition, the inotodiol derivative may be synthesized by adding the *Candida antarctica* lipase B in an amount of 400 parts by weight to 500 parts by weight with respect to 100 parts by weight of inotodiol. In this case, when the content of *Candida antarctica* lipase B is less than the above range, there is a problem in that the ester production efficiency is low since the esterification reaction does not sufficiently occur. On the other hand, when the content of *Candida antarctica* lipase B exceeds the above range, there is a problem in that the inotodiol derivative, which is a final product, cannot be synthesized with a high yield, which is not economical.

The pharmaceutical composition according to one aspect may be formulated for use in the form of oral formulations such as powders, granules, tablets, capsules, suspensions, emulsions, syrups and aerosols, preparations for external application, suppositories, and sterile injection solutions, according to general methods, and for formulation, may include suitable carriers, excipients or diluents that are commonly used in the preparation of a pharmaceutical composition.

The carriers, excipients or diluents may be various compounds or mixtures, including lactose, dextrose, sucrose, sorbitol, mannitol, xylitol, erythritol, maltitol, starch, acacia gum, alginates, gelatin, calcium phosphate, calcium silicate, cellulose, methyl cellulose, micro-crystalline cellulose, polyvinyl pyrrolidone, water, methylhydroxybenzoate, propylhydroxybenzoate, talc, magnesium stearate, mineral oil, and the like.

The pharmaceutical composition may be formulated using generally used diluents or excipients such as fillers, extenders, binders, wetting agents, disintegrating agents, and surfactants.

Another aspect provides a method of preventing or treating a liver X receptor (LXR)-mediated disease, the method including a step of administering inotodiol, a prodrug thereof, or a pharmaceutically acceptable salt thereof to a subject in need thereof.

Another aspect provides use of inotodiol, a prodrug thereof, or a pharmaceutically acceptable salt thereof for the preparation of a composition for preventing or treating a liver X receptor (LXR)-mediated disease.

The LXR-mediated disease is the same as described above.

The present specification provides a method for increasing reverse cholesterol transport and/or suppressing the progression of and promoting the alleviation of atherosclerosis.

The present specification also provides a method of treating diseases or disorders associated with a need to increase high density lipoprotein (HDL)-cholesterol levels, the method including administering an effective amount of inotodiol or a prodrug thereof to a mammal (particularly, a human) in need thereof.

The present specification also provides a method of treating diseases or disorders associated with a need to reduce low density lipoprotein (LDL)-cholesterol levels, the method including administering an effective amount of inotodiol or a prodrug thereof to a mammal (particularly, a human) in need thereof.

A solid preparation for oral administration may be prepared by mixing inotodiol, a prodrug thereof, or a pharmaceutically acceptable salt thereof with at least one excipient, for example, starch, calcium carbonate, sucrose or lactose, gelatin, or the like. In addition to simple excipients, lubricants such as magnesium stearate and talc may also be used.

Liquid preparations for oral administration may be suspensions, liquids for internal use, emulsions, syrups, and the like, and may include, in addition to commonly used simple diluents, such as water and liquid paraffin, various types of excipients, for example, a wetting agent, a sweetener, a flavoring agent, a preservative, and the like.

Preparations for parenteral administration include an aqueous sterile solution, a non-aqueous solvent, a suspension, an emulsion, a freeze-dried preparation, and a suppository. As the non-aqueous solvent and the suspension, propylene glycol, polyethylene glycol, a vegetable oil such as olive oil, and an injectable ester such as ethyl oleate may be used. As suppository bases, Witepsol, Macrogol, Tween 20, cacao butter, laurin butter, glycerol gelatin, and the like may be used.

A suitable dose of the pharmaceutical composition according to one aspect varies depending on conditions and body weights of patients, severity of disease, types of drugs, administration route, and administration time, but may be appropriately selected by those of ordinary skill in the art. However, to obtain desired effects, the pharmaceutical composition may be administered in an amount of 0.0001 mg/kg to 2,000 mg/kg, preferably 0.001 mg/kg to 2,000 mg/kg, daily. The pharmaceutical composition may be administered once or multiple times a day. The dosage is not intended to limit the scope of the present disclosure.

The pharmaceutical composition according to one aspect may be administered to mammals such as rats, mice, livestock, and humans via various routes. Examples of all administration methods may include oral injection, rectal or intravenous injection, muscular injection, subcutaneous injection, and intrauterine epidural injection or intracerebroventricular injection.

Another aspect provides a cosmetic composition for the prevention or amelioration of liver X receptor (LXR)-mediated skin conditions, including inotodiol, a prodrug thereof, or a pharmaceutically acceptable salt thereof as an active ingredient.

The LXR-mediated skin conditions are the same as described above.

The cosmetic composition may be, for example, a softening lotion, a nutritional lotion, a massage cream, a nutrient cream, an essence, a pack, a gel, an ampoule, or skin-adhesive cosmetic formulation.

The ingredients included in the cosmetic composition may include, in addition to the active ingredient, ingredients commonly used in cosmetic compositions, for example, general adjuvants and carriers such as a stabilizer, a solubilizer, a vitamin, a pigment, and a flavoring agent.

Another aspect provides a health functional food for the prevention or amelioration of a liver X receptor-mediated disease, including inotodiol, a prodrug thereof, or a pharmaceutically acceptable salt thereof as an active ingredient.

In the health functional food according to one aspect, when the compound is used as an additive for the health functional food, the composition may be directly added or may be used in combination of other foods or food ingredients, and may be appropriately used according to a general method. The amount of the active ingredient to be mixed may be appropriately determined according to the purpose of use such as prevention, health, or treatment.

Formulations of the health functional food may be not only in the form of powder, granules, pills, tablets, and capsules, but also in the form of general foods or beverages.

The type of food is not particularly limited, and examples of foods to which the substance may be added may include meat, sausage, bread, chocolate, candies, snacks, confectioneries, pizza, ramen, other noodles, gums, dairy products including ice cream, various soups, beverages, tea, drinks, alcoholic beverages, and vitamin complexes, and may include all foods in a general sense.

Generally, for the preparation of foods or beverages, the compound may be added in an amount of 15 parts by weight or less, preferably 10 parts by weight or less, with respect to 100 parts by weight of raw materials. However, in the case of long-term ingestion for health and hygienic purposes or for health control purposes, the amount may be below the above range, and since there is no safety problem in that a fraction from a natural substance is used, the active ingredient may also be used in an amount above the range.

In the health functional food according to one aspect, a beverage may contain additional ingredients such as various flavoring agents or natural carbohydrates as in general beverages. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As the sweetener, a natural sweetener such as a thaumatin or *stevia* extract, a synthetic sweetener such as saccharin or aspartame, or the like may be used. The proportion of the natural carbohydrates may range from about 0.01 g to 0.04 g, preferably about 0.02 g to 0.03 g, with respect to 100 mL of the beverage according to the present disclosure.

In addition to the above ingredients, the health functional food according to one aspect may include various nutritional supplements, vitamins, electrolytes, flavors, colorants, pectic acid and salts thereof, alginic acid and salts thereof, organic acids, a protective colloidal thickener, a pH adjuster, a stabilizer, a preservative, glycerin, alcohols, and a carbonating agent used in carbonated beverages. In addition, a composition for improving sleep of the present disclosure may contain flesh for the preparation of natural fruit juice, fruit juice beverages, and vegetable beverages. These ingredients may be used alone or a combination thereof may be used. The proportion of these additives is not limited, but the amounts of the additives generally range from 0.01 parts by weight to 0.1 parts by weight with respect to 100 parts by weight of the health functional food of the present disclosure.

Advantageous Effects of Disclosure

Inotodiol or a prodrug thereof according to one aspect has LXR beta-specific agonist activity, and thus not only has remarkable stability compared to other LXR agonists, but can also be effectively used in the treatment of LXR-mediated diseases, such as a neurodegenerative brain disease, an autoimmune disease, NASH, and NAFLD.

BRIEF DESCRIPTION OF DRAWINGS

FIG. 6 illustrates graphs showing the results of confirming that inotodiol according to an embodiment increases the expression of genes related to the suppression of neurodegenerative brain diseases, in which:

MODE OF DISCLOSURE

Hereinafter, exemplary examples will be described to aid in understanding of the present disclosure. However, the following examples are provided merely to facilitate the understanding of the present disclosure and are not intended to limit the scope of the present disclosure.

Example 1. In Vivo Analysis of Effect of Inotodiol on LXR-Related Factors

The effect of inotodiol on Abca1, Srebf1_1C, AQP1, and ApoE1, which are LXR-related markers, was analyzed.

First, an inotodiol emulsion for administration at a dose of 4 mg/kg was prepared. Specifically, an emulsion was prepared by mixing inotodiol with 10% of olive oil (Monini, Classico extra virgin olive oil), 0.5% of tween 80, and sterile water. Subsequently, each 0.15 mL of the prepared emulsion was administered to BALB/cAnNTacSam (Sam Taco Bio Korea Co., Ltd.) for 5 days. After 5 days of administration, mice were euthanized, and then spleen, lung, liver and peritoneal cell samples were isolated.

Next, to perform qPCR on the isolated samples, total RNA was extracted using a Bead™ Total RNA Prep Kit (BioFACT™) sample. Thereafter, primers for Abca1, Srebf1_1C, AQP1, and ApoE1 were used, the reaction reagent for qPCR was 2× Real-Time PCR Master Mix (BioFACT™), and the equipment used for qPCR was AriaMx Real-time PCR. The qPCR conditions were as follows: at 95° C. for 15 minutes, and 50 cycles at 95° C. for 20 seconds, 55° C. for 30 seconds, and 72° C. for 0.5-1 min/kb, and for the melting curve, 1 cycle was performed at 95° C. for 30 seconds, 65° C. for 30 seconds, and 95° C. for 30 seconds, and relative mRNA expression was measured. An untreated control was used as a control, and the results thereof are shown in FIGS. 1 to 4.

Figure 1:
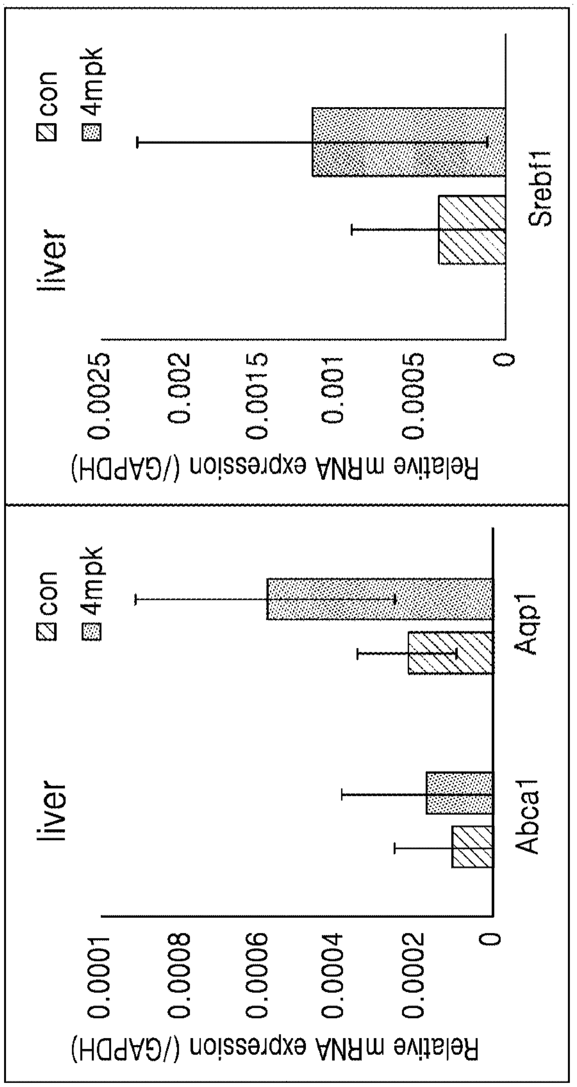
FIG. 1 is a graph showing that inotodiol according to an embodiment is an LXR-β-specific agonist in a liver sample.

FIG. 1 is a graph showing that inotodiol according to an embodiment is an LXR-β-specific agonist in a liver sample.

Figure 2:
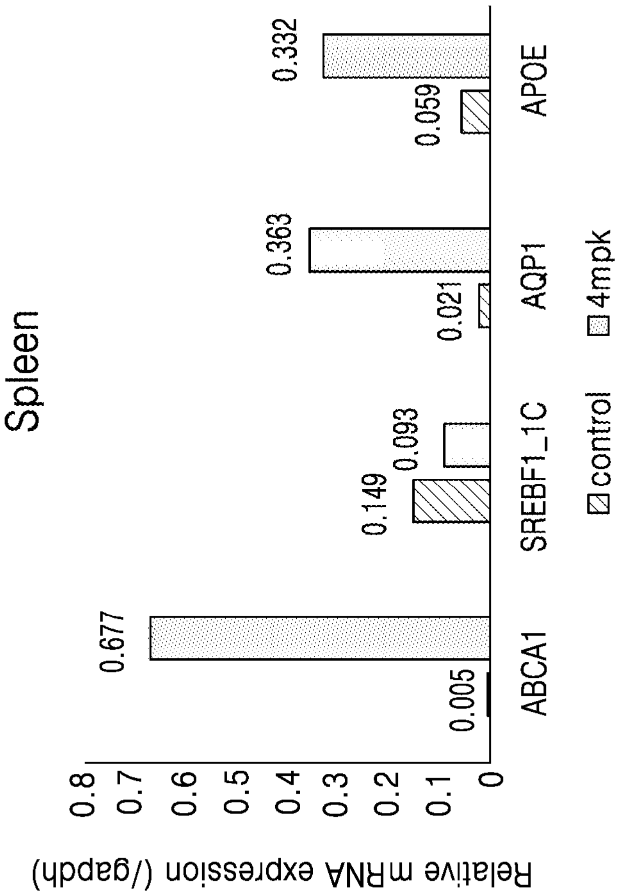
FIG. 2 is a graph showing that inotodiol according to an embodiment is an LXR-β-specific agonist in a spleen sample.

FIG. 2 is a graph showing that inotodiol according to an embodiment is an LXR-β-specific agonist in a spleen sample.

Figure 3:
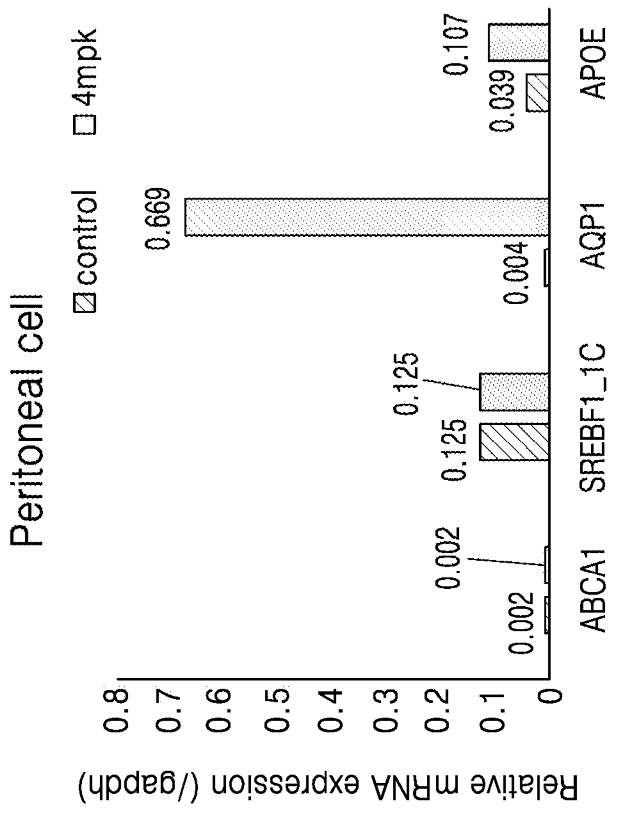
FIG. 3 is a graph showing that inotodiol according to an embodiment is an LXR-β-specific agonist in a peritoneal cell sample.

FIG. 3 is a graph showing that inotodiol according to an embodiment is an LXR-β-specific agonist in a peritoneal cell sample.

Figure 4:
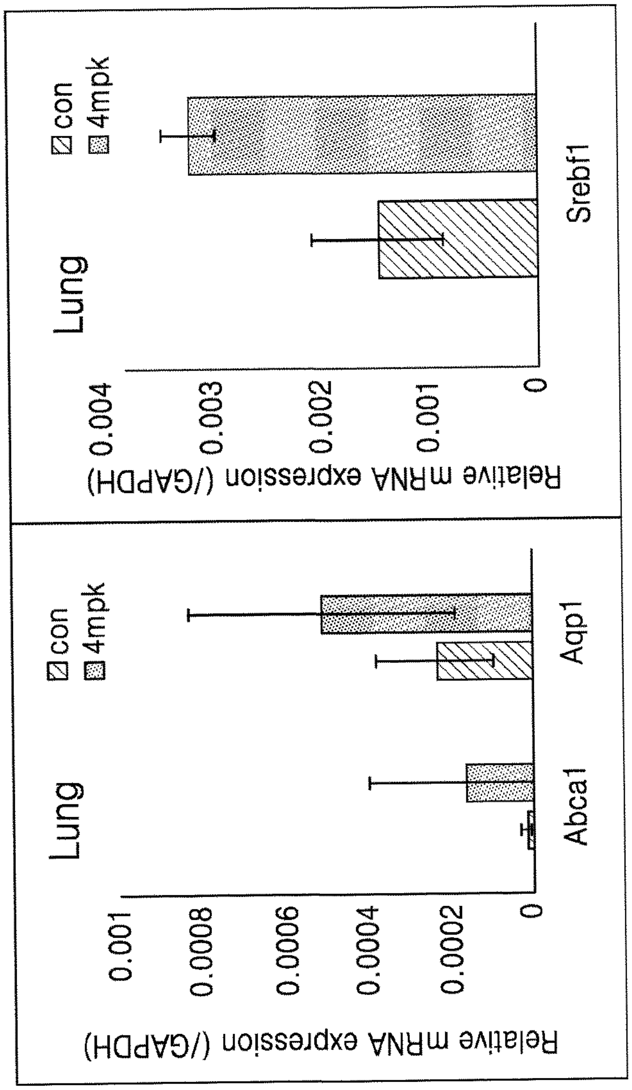
FIG. 4 is a graph showing that inotodiol according to an embodiment is an LXR-β-specific agonist in a lung sample.

FIG. 4 is a graph showing that inotodiol according to an embodiment is an LXR-β-specific agonist in a lung sample.

Figure 5:
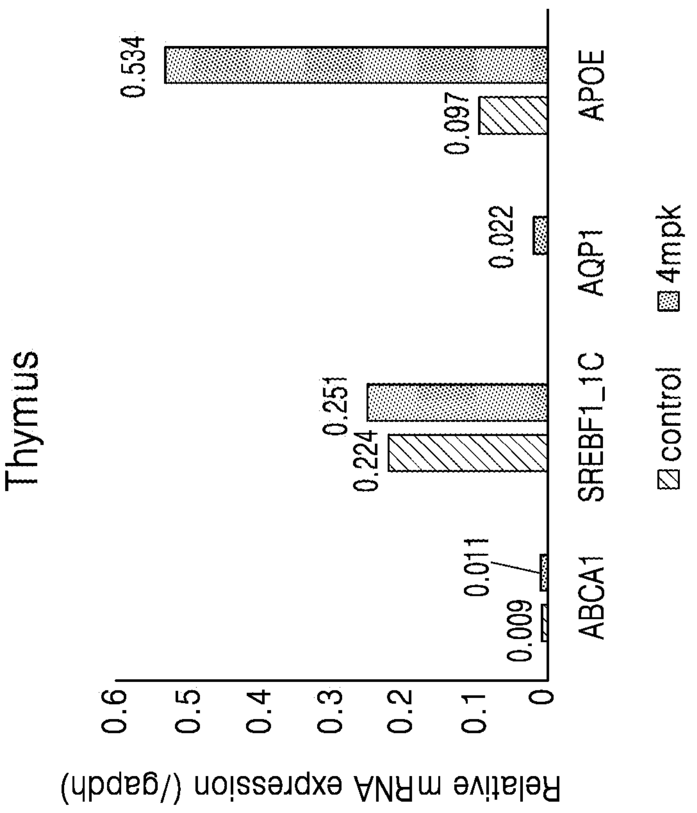
FIG. 5 is a graph showing that inotodiol according to an embodiment is an LXR-β-specific agonist in a thymus sample.

FIG. 5 is a graph showing that inotodiol according to an embodiment is an LXR-β-specific agonist in a thymus sample.

As illustrated in FIGS. 1 to 5, it can be seen that inotodiol according to an embodiment increases the expression of Abca1, AQP1, Srebf1, and ApoE1 in various samples.

These results indicate that inotodiol activates the transcriptional regulatory function of Abca1, AQP1, Srebf1, and ApoE1, which are related genes, by binding to LXRs.

In addition, it is known that generally, in the liver, LXR-α is expressed at a high level and LXR-β is expressed at a low level. Thus, there was no significant increase in the expression of Srebf1, which is specifically regulated by LXR-α, among the above markers, in a liver sample, and there was a significant increase in the expression of AQP1, which is regulated by LXR-β, from which it can be seen that inotodiol does not bind well to LXR-α and acts as an agonist by more specifically binding to LXR-β.

Therefore, these results not only mean that inotodiol can be effectively used in the treatment of LXR-mediated diseases, such as atherosclerosis, Alzheimer's disease, NASH, NAFLD, metabolic diseases, and dermatitis, but also means that, since inotodiol is specific to LXR-β, inotodiol has more safety compared to other LXR agonists.

Example 2. In Vivo Safety Analysis of Inotodiol

As in Example 1, to confirm that inotodiol is a safe LXR-β agonist, liver toxicity in mice was evaluated. If inotodiol is a LXR-α agonist, inotodiol overexpresses Srebf1 in the liver, thereby inducing fatty liver. Selectivity for LXRs and safety of inotodiol were evaluated through a two-week mouse toxicity test.

Specifically, the inotodiol emulsion was orally administered to male and female ICR mice in an amount of 0.0 mg/kg (group 1), 5.0 mg/kg (group 2), and 20 mg/kg (group 3) once a day for 2 weeks. For reference, a suitable dose of inotodiol for the treatment of asthma and food allergy, and the like is predicted to be 4.5 mg/kg to 5.0 mg/kg. As a control, 100% olive oil was administered. No signs of abnormal health were found in all subjects used in the experiment, and all surviving animals were euthanized after isoflurane anesthesia 15 days after administration, and then liver tissue was extracted and total fat content was analyzed. The results thereof are shown in Table below. As summarized in Table 1, there were no significant changes in total fat content of the liver in both male and female mice, not only at a dose of 5 mg/kg but also at a dose of 20 mg/kg of inotodiol.

TABLE 1

| Animal No. | | Total fat (%) in mouse liver | | | | | |
|---|---|---|---|---|---|---|---|
| | | Female | | | Male | | |
| # | | Group 1 | Group 2 | Group 3 | Group 1 | Group 2 | Group 3 |
| 1 | Analysis 1 | 3.07 | 4.42 | 3.16 | 2.87 | 3.19 | 3.36 |
| | Analysis 2 | 3.26 | 3.82 | 3.23 | 3.29 | 3.17 | 3.41 |
| 2 | Analysis 1 | 2.36 | 2.85 | 4.77 | 4.16 | 3.18 | 2.99 |
| | Analysis 2 | 2.27 | 3.09 | 4.62 | 3.28 | 3.43 | 2.93 |
| 3 | Analysis 1 | 3.39 | 2.96 | 4.01 | 3.19 | 3.39 | 3.38 |
| | Analysis 2 | 3.51 | 3.08 | 4.03 | 2.85 | 3.25 | 3.52 |
| 4 | Analysis 1 | 3.97 | 2.80 | 3.49 | 3.57 | 3.48 | 3.44 |
| | Analysis 2 | 3.91 | 2.72 | 3.49 | 3.38 | 3.47 | 3.47 |
| 5 | Analysis 1 | 3.08 | 3.45 | 2.69 | 2.73 | 2.83 | 3.07 |
| | Analysis 2 | 3.07 | 3.57 | 2.94 | 2.79 | 2.72 | 3.10 |
| 6 | Analysis 1 | 2.48 | 3.03 | 3.09 | 3.32 | 2.86 | 3.23 |
| | Analysis 2 | 2.72 | 3.10 | 3.19 | 3.08 | 3.78 | 3.30 |
| | Average | 3.09 | 3.24 | 3.56 | 3.21 | 3.23 | 3.27 |
| | std dev | 0.43 | 0.38 | 0.53 | 0.29 | 0.24 | 0.17 |
| | p-value | 0.496G1 Vs G2 | 0.195 G2 Vs G3 | 0.075 G1 Vs G3 | 0.896 G1 Vs G2 | 0.719 G2 Vs G3 | 0.657 G1 Vs G3 |

Example 3. In Vivo Analysis of Inotodiol Concentrations in Blood and Brain Tissue When inotodiol was administered to mice, the concentrations of inotodiol detected in blood and brain tissue of the mice were analyzed.

Specifically, 7-week-old Balb/c mice were supplied and acclimatized for 1 week, and then 4 mice per group were assigned to conduct experiments. Mice were grouped into: four controls not administered with inotodiol; and four groups administered with inotodiol. In the groups administered with inotodiol, 4.5 mg/kg of inotodiol was orally administered for 10 days. On day 11, the controls and inotodiol-administered mice were sacrificed, and blood and brain tissue samples were prepared.

First, to analyze the concentration of inotodiol in blood, 20 μL of serum was transferred to a 1.5 mL Eppendorf tube, and then inotodiol was extracted twice in ethanol. In each extraction step, 200 μL of ethanol was mixed with serum and the mixture was sonicated for 10 minutes, followed by centrifugation at 14000×g for 15 minutes.

To analyze the concentration of inotodiol in brain tissue, the whole brain was weighed and mixed with 10-fold (v/w) 100% ethanol, and then the mixture was sonicated and centrifuged.

After centrifugation, each residue was reconstituted with 0.5 mL of 60% methanol for solid phase extraction by using a C18 cartridge (Sep-Pak C18 3 cc Vac Cartridge, 200 mg adsorbent, Waters). Samples were loaded into cartridges and activated using methanol (6 mL), followed by conditioning with 60% methanol (6 mL). The cartridges were then washed with 6 mL of 60% methanol. Then, inotodiol was collected by eluting the cartridges with 100% methanol (3 mL) in glass tubes. After evaporation of each sample, the residue was dissolved in methanol and subjected to LC/MS analysis.

As a result, as shown in Table 2, inotodiol was not detected in brain tissue and blood in the controls, and, in the inotodiol-administered groups, an average of 151.7±21.3 ng/g of inotodiol was detected in brain tissue, and an average of 12.1±1.3 ng/g of inotodiol was detected in blood, from which it was confirmed that inotodiol was detected in the brain about 12 times greater than that in blood.

These results demonstrate that inotodiol is effectively delivered to the brain of an animal.

TABLE 2

| | Inotodiol concentration (ng/g) | Inotodiol-administered | Inotodiol concentration (ng/g) | |
|---|---|---|---|---|
| Control | Brain/blood | group | Brain | Blood |
| 1 | Not detected | 1 | 161.4 | 12.2 |
| 2 | Not detected | 2 | 177.1 | 10.5 |
| 3 | Not detected | 3 | 133.3 | 14.2 |
| 4 | Not detected | 4 | 135.0 | 11.8 |
| Average | Not detected | Average | 151.7 ± 21.3 | 12.1 ± 1.3 |

Example 4. In Vivo Analysis of Expression of Genes Related to Neurodegenerative Brain Diseases in Brain Tissue When inotodiol was administered to mice, the expression of ABCA1 and APOE in brain tissue, which are genes related to neurodegenerative brain diseases, was analyzed.

Specifically, as in Example 3, controls and inotodiol-administered mouse groups were prepared, and then, to extract total RNA, first, 50 mg of brain tissue samples were quantified, and then cells were crushed using a mortar. 1 mL of Trizol was dispensed into each crushed sample and mixed by vortexing. Then, 0.2 mL of chloroform was dispensed and a reaction was allowed to occur therein at room temperature for 3 minutes. The reaction product was centrifuged at 12,000 rpm and 4° C. for 15 minutes, and then only the transparent supernatant was transferred to a new tube. Thereafter, 0.5 mL of isopropyl alcohol was dispensed, and then a reaction was allowed to occur therein at room temperature for 10 minutes. The resultant was centrifuged 12,000 rpm and 4° C. for 10 minutes, and then the supernatant was completely removed, and impurities were removed using 1 mL of 75% ethanol. After centrifugation at 7,500 rpm and 4° C. for 5 minutes, 75% ethanol was added, followed by centrifugation, and the supernatant was removed as much as possible, followed by drying on a 55° C. heat block for about 5 minutes. Each sample was dissolved using DEPC water, and then total RNA was quantified to 1000 ng/μL using Nanodrop, and cDNA synthesis was performed using primeScript RT Master Mix (Takara Korea). Real-time PCR was performed using Smartgene Sybr Green Q-PCR master mix (Samjeong Bioscience) and primers specific to the APOE and ABCA1 genes.

As a result, as illustrated in FIG. 6, the ABCA1 and APOE genes were highly expressed in brain tissue in the group administered with inotodiol (Ino (10 mpk)) compared to the control (Naïve) not administered with inotodiol. ABCA1 is known to activate APOE and suppress inflammation in the brain, and the activation of APOE is known to eliminate amyloid beta.

Figure 6A:
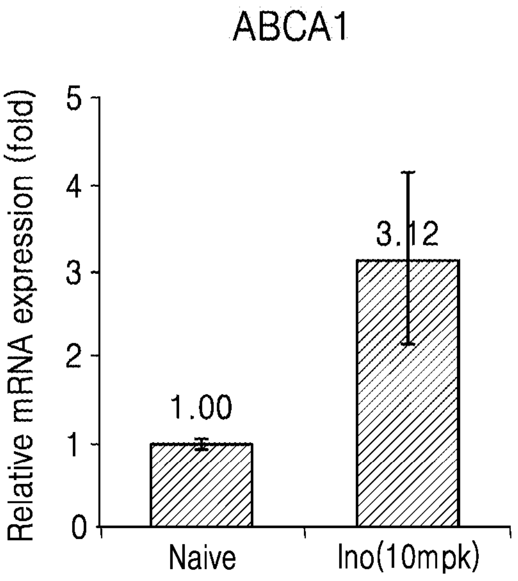
FIG. 6A is a graph showing the results of confirming that inotodiol according to an embodiment increases the expression of ABCA1, which is a gene related to the suppression of degenerative brain diseases.
Figure 6B:
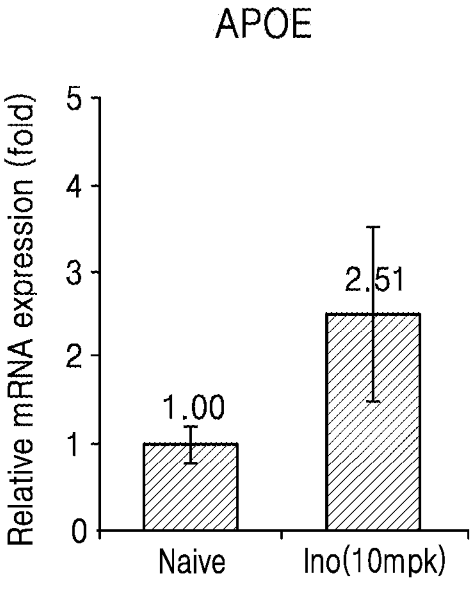
FIG. 6B is a graph showing the results of confirming that inotodiol according to an embodiment increases the expression of APOE, which is a gene related to the suppression of degenerative brain diseases.

FIG. 6 illustrates graphs showing the results of confirming that inotodiol according to an embodiment increases the expression of genes related to the suppression of degenerative brain diseases, in which:

FIG. 6A is a graph showing the results of confirming that inotodiol according to an embodiment increases the expression of ABCA1, which is a gene related to the inhibition of degenerative brain diseases; and FIG. 6B is a graph showing the results of confirming that inotodiol according to an embodiment increases the expression of APOE, which is a gene related to the suppression of degenerative brain diseases.

Therefore, these results indicate that inotodiol promotes the release and degradation of amyloid beta and has the effect of lowering an inflammatory response of microglial cells, which indicates that inotodiol can be effectively used in the treatment of neurodegenerative brain diseases.

Example 5. In Vivo Confirmation of Therapeutic Effect of Inotodiol on Rheumatoid Arthritis and Psoriasis To confirm whether inotodiol is effective in treating rheumatoid arthritis when administered to mice, bovine type II collagen was administered to male DBA/1J mice to induce arthritis, and then inotodiol was orally administered.

Specifically, after a 6-day acclimatization period, while bovine type II collagen (2 mg/mL in 0.05 mol/L acetic acid; Chondrex, Inc., U.S.A.) was slowly mixed with the same amount of a complete Freund's adjuvant (Chondrex, Inc., U.S.A.), an emulsion was prepared using a homogenizer at the same time, followed by secondary immunization using a method of subcutaneously administering 0.05 mL/head of the emulsion to the tail of each mouse by using a disposable syringe, thereby inducing arthritis.

Six mice with no abnormalities in health conditions and close to average weight were selected from mice in which arthritis was not induced, and used as a normal control, and 18 mice with no abnormalities in health conditions and close to average weight were selected from mice in which arthritis was induced. The 18 mice were grouped into 6 mice per group so that the average body weights of the respective groups were equal to each other. The mice with induced arthritis were grouped into: a group not administered with inotodiol; a group administered with 4 mg/kg of inotodiol; and a group administered with 10 mg/kg of inotodiol. Administration was forcibly performed intragastrically using a disposable syringe with a sonde for oral administration once a day for 4 weeks, a total of 28 times from the start of administration.

Arthritis symptoms were observed with the naked eye twice a week for 4 weeks from the start of administration. The knees, ankles and insteps of all legs of each mouse were observed with the naked eye, and the arthritic index was recorded on the basis of macroscopic arthritic index evaluation criteria in Table 3 below. The macroscopic arthritic score (maximum score=16) of each individual was calculated by summing up the arthritic indices for all legs of each mouse.

TABLE 3

| Severity score | Degree of inflammation |
|---|---|
| 0 | No symptoms of erythema and edema |
| 1 | Mild but distinct erythema and edema of the ankles, or distinct erythema and edema confined to individual toes (regardless of how many toes are affected) |
| 2 | Moderate erythema and edema of the ankles |
| 3 | Severe erythema and edema of the entire foot, including toes |
| 4 | Maximally inflamed limb with involvement of multiple joints |

Figure 7:
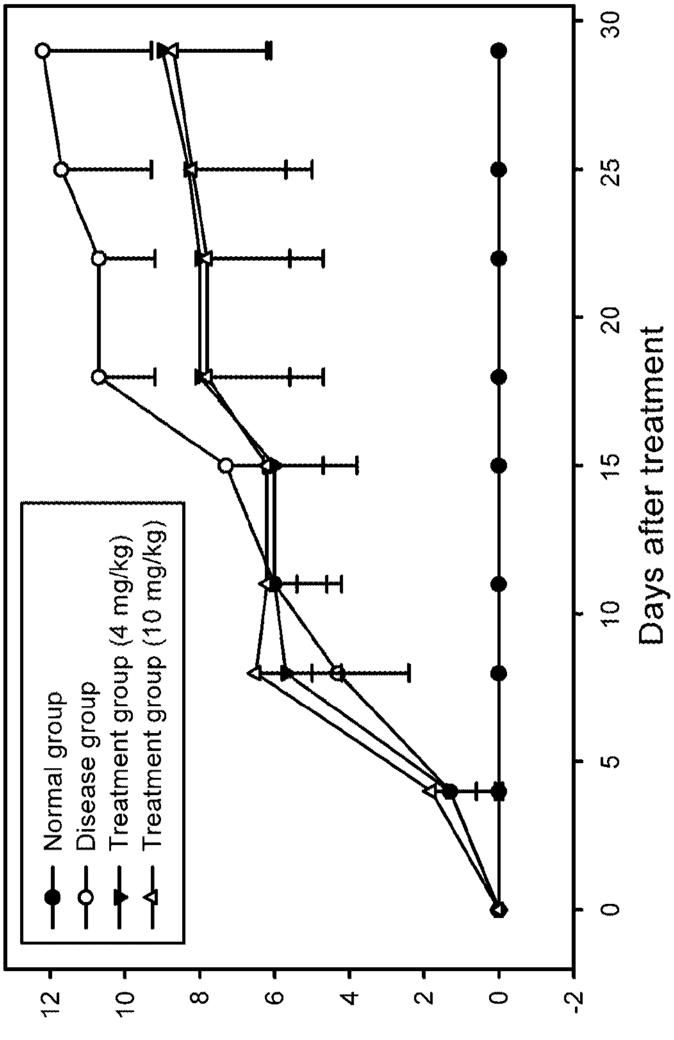
FIG. 7 is a rheumatoid arthritic score group showing that inotodiol according to an embodiment is effective in rheumatoid arthritis.

As a result, as illustrated in FIG. 7, it was confirmed that the arthritic score was lower in the arthritic animals administered with inotodiol compared to the arthritic animals not administered with inotodiol.

FIG. 7 is a rheumatoid arthritic score graph showing that inotodiol according to an embodiment is effective in rheumatoid arthritis.

Next, the expression of TNF-α, which is a factor that activates inflammation, was confirmed.

Specifically, a primary antibody (Biolegend) capable of specifically binding to mouse TNF-α was diluted in a coating buffer and 100 μl thereof was dispensed into a plate at a concentration of 0.5-8 μg/mL, and then stored at 4° C. for 18 hours. Then, the coating buffer was removed, followed by washing three times with 200 μL of washing buffer (0.05% Tween20/PBS). To prevent non-specific binding, a reaction with 200 μL of a blocking solution (1% BSA/PBS) was allowed to occur at room temperature for 1 hour. Washing was performed three times using a washing buffer. A standard material (Biolgend) and each sample were diluted using a blocking solution, and then 100 μL of each thereof was dispensed, and a reaction was allowed to occur therein at room temperature for 2-4 hours. Washing was performed three times using a washing buffer. A secondary antibody (biotin-labeled detection antibody, biolegend) was diluted to 0.25-2 μg/mL using a blocking solution, and then 100 μl thereof was dispensed and a reaction was allowed to occur therein at room temperature for 1 hour. Washing was performed three times using a washing buffer. Avidin-Horseradish peroxidase (Biolegend) was diluted 1/1000 times using a blocking solution, then 100 μL thereof was dispensed and a reaction was allowed to occur therein at room temperature for 30 minutes. Washing was performed 5 times using a washing buffer. 100 μL of TMB (Biolegend) was dispensed, and then a reaction was allowed to occur therein for 4-30 minutes. When the color change occurred, 100 μL of 2N $H_2SO_4$ was dispensed to stop the reaction. An ELISA plate was examined at 450 nm using an EPOCH microplate reader (Biotek).

Figure 8:
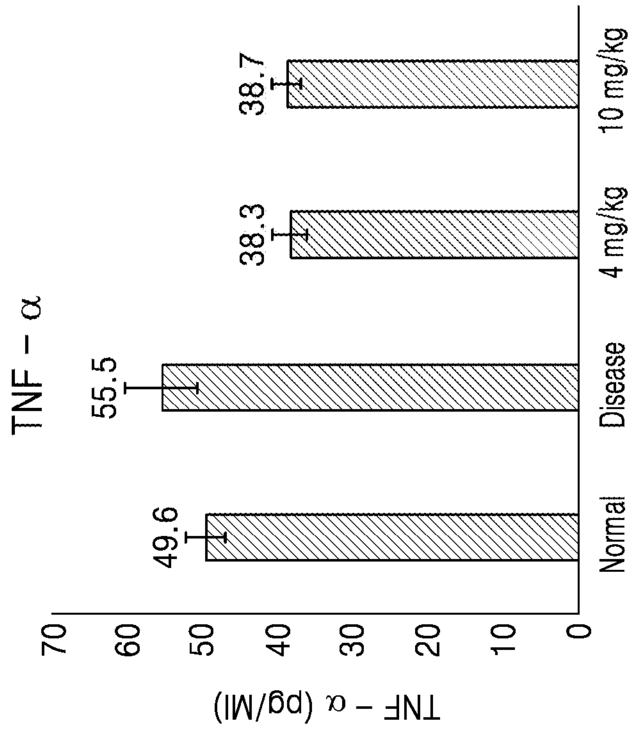
FIG. 8 is a graph showing that inotodiol according to an embodiment inhibits TNF-α expression.

As a result, as illustrated in FIG. 8, it was confirmed that TNF-α was expressed at a lower level in arthritic animals administered with inotodiol.

FIG. 8 is a graph showing that inotodiol according to an embodiment inhibits TNF-α expression.

The above results indicate that inotodiol can be effectively used not only in the treatment of rheumatoid arthritis but also in the treatment of psoriasis.

The above description of the present disclosure is provided only for illustrative purposes, and it will be understood by those of ordinary skill in the art to which the present disclosure pertains that the disclosure can be embodied in various modified forms without departing from the technical spirit or essential characteristics thereof. Thus, the embodiments described herein should be considered in an illustrative sense only and not for the purpose of limitation.

The invention claimed is:

1. A method of treating Alzheimer's disease or rheumatoid arthritis, the method comprising administering inotodiol or a prodrug thereof to a subject in need thereof, wherein the prodrug is inotodiol-acetate diester, inotodiol-butyrate diester, inotodiol-caprylate diester or inotodiol-myristate diester, and the inotodiol or the prodrug thereof is a LXR agonist that upregulates the expression or activity of the LXR.

2. The method of claim 1, wherein the prodrug is inotodiol-butyrate diester.

3. The method of claim 1, wherein the prodrug is inotodiol-caprylate diester.

4. The method of claim 1, wherein the prodrug is inotodiol-myristate diester.

5. The method of claim 1, wherein the prodrug is inotodiol-acetate diester.

* * * * *